United States Patent [19]

Dubowik et al.

[11] Patent Number: 5,280,091

[45] Date of Patent: Jan. 18, 1994

[54] EPOXY RESINS CURED WITH MIXED METHYLENE BRIDGED POLY(CYCLOHEXYL-AROMATIC)AMINE CURING AGENTS

[75] Inventors: David A. Dubowik, Kempton; Peter A. Lucas, Allentown; Andrea K. Smith, Bethlehem, all of Pa.

[73] Assignee: Air Products and Chemicals, Inc., Allentown, Pa.

[21] Appl. No.: 832,263

[22] Filed: Feb. 7, 1992

[51] Int. Cl.$^5$ ............................................. C08G 59/50
[52] U.S. Cl. .................................. 525/504; 525/510; 528/120; 528/122; 528/361; 528/407
[58] Field of Search ............... 528/122, 120, 361, 407; 525/504, 510

[56] References Cited

U.S. PATENT DOCUMENTS

| | | | |
|---|---|---|---|
| 2,511,913 | 6/1950 | Greenlee | 525/510 |
| 2,817,644 | 12/1957 | Shokal et al. | 260/47 |
| 2,981,711 | 4/1961 | Meyer et al. | 260/31.2 |
| 2,999,826 | 9/1961 | Peerman et al. | 260/18 |
| 3,321,438 | 5/1967 | Brooker et al. | 260/47 |
| 3,629,181 | 12/1971 | Heer et al. | 260/31.8 |
| 4,226,737 | 10/1980 | Kluger et al. | 252/182 |
| 4,321,353 | 3/1982 | Kluger et al. | 528/120 |
| 4,447,586 | 5/1984 | Shimp | 525/504 |
| 4,946,925 | 8/1990 | Strohmayer | 528/122 |

FOREIGN PATENT DOCUMENTS

| | | | |
|---|---|---|---|
| 53-9639 | 4/1978 | Japan . | |
| 1536808 | 12/1978 | United Kingdom | 87/40 |

*Primary Examiner*—Frederick Krass
*Attorney, Agent, or Firm*—Russell L. Brewer; James C. Simmons; William F. Marsh

[57] ABSTRACT

This invention pertains to epoxy resins having increased chemical resistance to solvents, and good cured mechanical properties which are prepared by curing the epoxy resins with a curing agent comprising a mixture of methylene bridged poly(cyclohexyl-aromatic)amines. The methylene bridged poly(cyclohexyl-aromatic)amine curing agents are the residue obtained from the distillation of a mixture of poly(cyclohexylaromatic)amines formed by the hydrogenation of crude methylenedianiline or crude di(4-amino-3-methylcyclohexyl)methane.

31 Claims, No Drawings

EPOXY RESINS CURED WITH MIXED METHYLENE BRIDGED POLY(CYCLOHEXYL-AROMATIC)AMINE CURING AGENTS

TECHNICAL FIELD

This invention pertains to epoxy resins cured with mixed methylene bridged poly(cyclohexyl-aromatic)amines and a process for producing such epoxy resins.

BACKGROUND OF THE INVENTION

Aliphatic and aromatic polyamines have been used in the past for curing epoxy resins. It is well known that the aliphatic amines have accelerated reaction with epoxy resins and react at a faster rate than do aromatic polyamines. Aliphatic polyamines can effect cure at room temperature while aromatic polyamines generally require more rigorous cure conditions or additives which act as accelerators.

Epoxy resins by their very nature are generally chemically resistant and have utility as coatings, encapsulating agents and composite matrices. Even so, the properties of epoxy resins also are affected by the type of curing agent used for curing the polyepoxide. Cycloaliphatic curatives permit rapid, subambient or low temperature cure cycles but also leave residual NH functionality in the cured epoxy resin which may react with ambient carbon dioxide to form surface carbamates. These carbamates lead to water spotting and poor interfacial adhesion and, as a result, the resins may be unsuited for subsequent coating and architectural applications. In addition, either incompatibility or rapid cures effected by cycloaliphatic polyamines often result in incomplete incorporation of the curative in the final epoxy matrix. Amine exudation and degradation of surface and interfacial properties of the epoxy resin may result because of such lack of incorporation. Aromatic amines, on the other hand, because they are less basic and nucleophilic than their cycloaliphatic counterparts, do not react with carbon dioxide to form surface carbamates and thus do not suffer from the inadequacies imparted by cycloaliphatic amines. In addition, chemical resistance of epoxy resins cured with aromatic amines is superior to that of cycloaliphatic cured systems. However, there are problems associated with the use of common aromatic polyamines. One problem associated with such common aromatic diamines relates to their hygienic considerations in the workplace. Many single ring and double ring diamines are toxic or carcinogenic.

Representative patents which describe epoxy resins and the utilization of aromatic and cycloaliphatic amines as curatives, therefore are as follows:

U.S. Pat. No. 2,817,644 discloses a process for curing and resinifying polyepoxides by reacting the polyepoxides with hydrogenated aromatic primary or secondary amines. Examples of aromatic amines which could be hydrogenated to form the cycloaliphatic counterparts include p,p'-methylenedianiline, 2,4-diaminotoluene, and the like. The hydrogenated aromatic amines provide epoxy resin products having excellent hardness and excellent resistance to solvents and water.

U.S. Pat. No. 2,981,711 discloses the use of amines as hardening agents for epoxy resins formed by the reaction of a polyglycidylether of a polyhydric phenol with epichlorohydrin. Both aromatic and cycloaliphatic amines are represented and these include para,para'-diaminodiphenylmethane, para,para'-diaminodiphenylpropane, and cycloaliphatic amines include diaminodicyclohexylmethane (often referred to as PACM), diaminodicyclohexylpropane and diaminotricyclohexylmethane.

U.S. Pat. No. 2,999,826 discloses epoxy resins cured with a polyamide adduct incorporating both aliphatic and aromatic amines. The polyamide adduct when used to cure the epoxy resins provides an epoxy product which has a balance of properties associated with cycloaliphatic and aromatic curatives. More specifically, these epoxy resins exhibit great toughness, excellent resistance to impact and excellent machinability. Volatility of the adduct is much lower than the corresponding amines and hygienic safety is improved. The patentees do point out in the background portion of the invention that when mixtures of aliphatic and aromatic polyamines were simply blended together and reacted with epoxy resins, the resulting product was quite brittle and had poor machining characteristics. In addition the simple blending of the aliphatic and aromatic amines did not overcome the volatility and toxicity of the blend.

U.S. Pat. Nos. 4,226,737 and 4,321,353 disclose epoxy curatives which are methylene bridged polycycloaliphatic polyamines represented by the structural formulas:

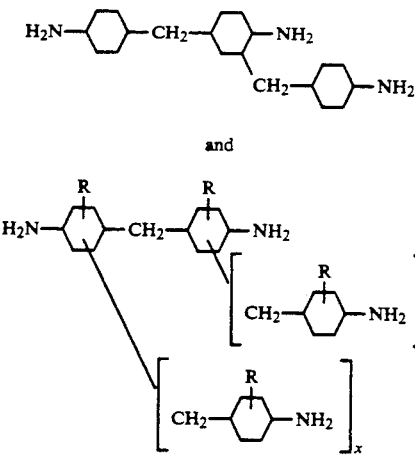

wherein x and y are from 0-2 and the sum of x plus y is from 1 to 4. Typically the curative consists essentially of from 50 to 75% of the methylene bridged tricyclohexyltriamine and from 15 to 30% of the tetracyclohexyltetramine. The patentees report that the curing agents overcome substantial problems encountered with prior art amine curatives in that they have lower volatility and reduced toxicological properties. In addition the patentees report higher glass transition temperatures, and thus improved thermal properties, can be achieved vis-a-vis 1,2-cyclohexanediamine.

U.S. Pat. No. 3,321,438 discloses aliphatic and cycloaliphatic amines, including piperazines as curing agents for fluidized bed epoxy coating compositions. Examples of aliphatic amines include diethylenetriamine and triethylenetetramine; cycloaliphatic diamines include di(4-aminocyclohexyl)methane, di(3-methyl-4-aminocyclohexyl)methane and the N-substituted derivatives.

U.S. Pat. No. 3,629,181 discloses various cycloaliphatic and cycloaliphatic-aliphatic di-primary amines for use in preparing adducts as curing agents for polyepoxide resin systems. Representative amines include 1,4-diamino-3,6-diethylcyclohexane; 2,2-di(4-aminocyclohexyl)propane which is commonly referred to as hydrogenated bisaniline A and 3-aminomethyl-3,5,5-trimethyl-1-cyclohexylamine, which is commonly referred to as isophoronediamine.

U.S. Pat. No. 4,447,586 discloses a process for producing polyepoxide resins by incorporating therein a metal fluoborate and a hindered aromatic amine curing agent. Examples of the hindered aromatic amines include diethyltoluenediamine, methylenebis(2,6-diisopropylaniline), methylenebis(2,6-diethylaniline) and methylenebis(2-methyl-6-ethylaniline).

U.S. Pat. No. 4,946,925 discloses various bridged bis(cyclohexylamine) derivatives as curing agents. Each cyclohexylamine group has two alkyl groups where the alkyl groups are in the 2 and the 5 positions and the amine groups are in the 4 position. Specific curing agents include 2,2',5,5'-tetramethylmethylenedicyclohexylamine and 2,2',5,5'-tetraethylmethylenedicyclohexylamine. The tetraalkyl substitution pattern in the bridged cyclohexylamine derivative provides for extended pot life by retarding activity of the amine as a curative and the tetraalkyl substitution also enhances thermal properties of the epoxy resin.

British Patent 1,536,808 discloses a process for the hydrogenation of methylene bridged aromatic amines, such as, methylenedianiline. The patentees suggest that it is well known that the mixed isomeric methylene bridged polycyclohexylpolyamines are useful as curing agents for vicinal epoxides.

SUMMARY OF THE INVENTION

This invention relates to polyepoxide resins cured with a mixture of methylene bridged poly(cycloaliphatic-aromatic)amines (sometimes referred to as "MPCA") and a process for preparing such polyepoxide resins. In the preparation of the MPCA mixture, a condensation product of formaldehyde and aniline or toluidine containing substantial amounts of oligomer is partially hydrogenated and the partially hydrogenated product separated by distillation. The heavier components of the distillation mixture or bottoms are represented by the formula:

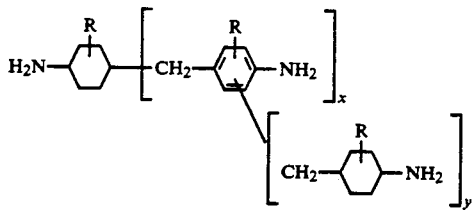

wherein R is hydrogen or methyl, x is 1-3, y is 0-2 and the sum of x and y is from 2 to 4.

An MPCA mixture contains substantial amounts of 3 ring and higher aliphatic-aromatic rings. Typically the weight ratio of 3 ring to 4 ring and higher aliphatic-aromatic ring components will be from 50 to 90 parts of the 3 ring component to 10 to 50 parts of the 4 ring and higher components. The ratio of cycloaliphatic rings to aromatic rings in said MPCA will range from 0.5 to 2:1, and preferably 1.3 to 1.9:1.

The utilization of the MPCA mixture of methylene-bridged poly(cycloaliphatic-aromatic) amines, as described above, overcomes major problems associated with prior art epoxy curatives and these advantages include:

an ability to produce epoxy coating compositions having excellent gloss and water spotting resistance;

an ability to formulate epoxy resin compositions with reduced environmental problems due to the low toxicity of the curing agent as compared to aromatic amines;

an ability to generate epoxy compositions having excellent thermal properties, chemical resistance, and mechanical properties including fracture toughness, flexibility, elongation, strength and so forth required for composites and for structural applications;

an ability to produce an epoxy resin having reduced resistance to amine exudation;

an ability to enhance part integrity for molding operations and minimize resin loss because of higher room temperature viscosity, and yet, on heating, the resin becomes less viscous and has excellent flowability; and, an ability to enhance throughput of molded products due to excellent reaction rates.

DETAILED DESCRIPTION OF THE INVENTION

Polyepoxides which can be cured using the methylene bridged poly(cyclohexyl-aromatic)amines of this invention include those polyepoxides having more than one epoxy group per molecule with the epoxy group typically being a terminal 1,2-epoxy group. The polyepoxides are well known and representative polyepoxides are described in U.S. Pat. Nos. 3,351,610, 4,447,586 and 4,946,925 which are incorporated by reference. Although both liquid and solid polyepoxides can be used, polyepoxides which are liquid are preferred. Examples of polyepoxides which are conventionally used include those which are based upon phenols and aliphatic polyols. Representative phenolic polyepoxides typically used include glycidyl polyethers of polyhydric phenols derived from a polyhydric phenol and epihalohydrin. The resulting polyepoxides generally will have an epoxide equivalent weight ranging from about 100 to 1,000. Epihalohydrins used in preparing the polyepoxides include epichlorohydrin and epibromohydrin and polyhydric phenols include resorcinol, hydroquinone, di(4-dihydroxyphenyl)methane, commonly referred to as bisphenol F; and, di(4-hydroxyphenyl)propane, commonly referred to as bisphenol A and novolacs where the phenolic groups are bridged via methylene groups. Of these polyhydric phenols, those based upon bisphenol A are the most common and preferred in the practice of this invention.

Aliphatic epoxides such as vinylcyclohexene dioxide; 3',4'-epoxy-cyclohexylmethyl-3,4-epoxy-cyclohexane carboxylate and liquid polyglycidyl ethers of polyalcohols such as 1,4-butanediol or polypropylene glycol can also be used.

Other types of polyepoxides which can be cured with the methylene bridged poly(cycloaliphatic-aromatic)amines and derivatives thereof are glycidyl polyesters prepared by reacting an epihalohydrin with an aromatic or aliphatic polycarboxylic acid. Polyepoxides utilizing glycidyl functionality from a glycidyl amine can also be used. This glycidyl functionality is provided by reacting a polyamine with epichlorohydrin.

The methylene bridged poly(cyclohexyl-aromatic)amines in the mixture used for producing curable polyepoxide resins are represented by the formula:

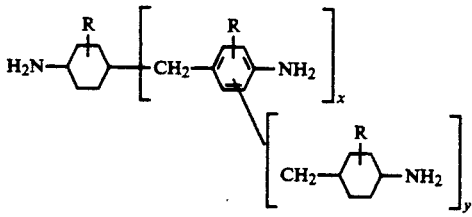

wherein x is from 1-3 and y is 0-2 and the sum of x and y is from 2 to 4.

The methylene bridged poly(cyclohexyl-aromatic)amines are known and can be synthesized in conventional manner, e.g., condensing aniline or toluidine with formaldehyde, followed by hydrogenation. The crude reaction product obtained with the condensation of aniline generally contains from about 15 to 50% by weight of the 3 ring and higher molecular weight oligomers with the balance being methylenedianiline.

Hydrogenation of the crude methylenedianiline or di(4-amino-3-methylphenyl)methane can be effected by well known processes using a hydrogenation catalyst. Typically a ruthenium or rhodium catalyst or mixture of the two catalysts is used to effect hydrogenation. Many of the impurities in crude methylenedianiline or di(4-amino-3-methylphenyl)methane act as poisons to hydrogenation catalysts and some precautions must be taken to effect hydrogenation. Conditions of hydrogenation will range from a hydrogen pressure of from 500 to 4000 psig and preferably 700-1500 psig and a temperature ranging from 150° to 250° C., preferably from 170° to 190° C. To convert substantially all of the methylenedianiline or di(4-amino-3-methylphenyl)methane to at least partially hydrogenated product, reaction times may extend for a period of 1 to 4 hours. Monitoring of the hydrogenation process by sampling is the best method of determining when the desired degree of hydrogenation is obtained. In the preferred low pressure process (700-1500 psig) from about 10 to 65% by weight of the hydrogenation reaction product (containing 2 ring components and the higher oligomers) is comprised of a mixture of methylene bridged poly(cycloaliphatic-aromatic)amines. In contrast, the high pressure process is capable of complete hydrogenation of the crude aromatic product. In that case, the reaction should be terminated after substantially all of the methylenedianiline or di(4-amino-3-methylphenyl)methane is converted to partially hydrogenated product and prior to complete hydrogenation of all of the aromatic rings of the 3 ring component. An example of a process for hydrogenating methylenedianiline and derivatives is shown in U.S. Pat. No. 4,754,070 and the process described therein is incorporated by reference.

In a distilled form, an MPCA containing distillation fraction substantially free of two ring components and substantially free of non elutables as determined by gas chromatographic analysis contains:

10-37% 2,4-di(4-aminocyclohexylmethyl)cyclohexylamine;
67-85% 2,4-di(4-aminocyclohexylmethyl)aniline;
0-20% 4,4'-di(4-aminocyclohexylmethyl)dicylohexylamine and,
5-14% partially hydrogenated trimethylenetetraaniline and analogs thereof.

In a partially distilled form, and therefore a form containing substantial amounts of two ring components but substantially free of non elutables, a typical MPCA containing curative as determined by gas chromatographic analysis (hereinafter sometimes referred to as "MPCA Blend") comprises the following components:

2-10% di(4-aminocyclohexyl)methane (PACM);
0.5-2% 4-aminocyclohexyl-4-hydroxycyclohexylmethane;
5-17% 4-(4'-aminobenzyl)cyclohexylamine; (ABCHA)
5-25% 2,4-di(4-aminocyclohexylmethyl)cyclohexylamine;
35-55% 2,4-di(4-aminocyclohexylmethyl)aniline;
0-15% 4,4'-di(4-aminocyclohexylmethyl)dicyclohexylamine; and,
3-8% partially hydrogenated trimethylenetetraaniline and analogs thereof.

The amine hydrogen equivalent of an MPCA containing mixture as described above containing the two ring components typically will range from 50 to 60 and preferably be within the range of from 54-56.

The methylene bridged poly(cyclohexyl-aromatic)amines can also be converted to epoxy adducts and used in that form as a curative for polyepoxides. To use the MPCA in such form, an excess of amine is reacted with the epoxide. The adduct containing unreacted amine hydrogens then can be reacted with a polyepoxide to produce a cured epoxy resin product. An example of such adduct is one where a diglycidylether of bisphenol A is reacted with the MPCA or the MPCA Blend in furfuryl alcohol.

The polyepoxides can be cured in conventional manner by effecting reaction with the methylene bridged poly(cyclohexyl-aromatic)amine. Typically the amount of methylene bridged poly(cyclohexyl-aromatic)amine curative which is reacted with the polyepoxide will range from a level of 0.6 to 1.7 times the stoichiometric or equivalent amount of polyepoxide resin present. Preferably, the level of methylene bridged poly(cyclohexylaromatic)amine to polyepoxide is from about 0.9 to 1.1 times the stoichiometric amount, stoichiometric being one equivalent weight of epoxide per equivalent weight of amine hydrogen.

Other polyamine curing agents can be used in combination with MPCA and these include aromatic polyamines such as diethyltoluenediamine, and methylenedianiline; and aliphatic amines such as di(4-aminocyclohexyl)methane (PACM), isophoronediamine, 1,3-xylylenediamine, and polyalkylenepolyamines such as diethylenetriamine and triethylenetetramine and the mixed methylene bridged poly(cyclohexylaromatic)amine, 4-(4'-aminobenzyl)cyclohexylamine (ABCHA). In many cases the amine functionality for curing is provided by a mixture of an aliphatic amine such as PACM or ABCHA or both. When a mixture of polyamines is used as the curative, the MPCA will range from 5 to 70% by weight of the curative. A polyamine mixture which has been found to be excellent comprises the MPCA and ABCHA or PACM or both in an amount of from 15-70% MPCA and from 30 to 85% by weight of 4-(4'-aminobenzyl)cyclohexylamine, di(4-aminocyclohexyl)methane or combinations thereof.

Conventional accelerators, plasticizers, fillers, glass and carbon fibers, pigments, solvents, etc. used in formulating epoxy coatings, mold compositions, lacquers, etc. can be used. Selection and amount of these additives is at the option of the formulator. The adjustment of cure temperatures and curing times for polyepoxide resins is within the discretion of the formulator. Representative accelerators which may be used, although not mandatory, include: boron trifluoride amine complexes and metal fluoroborate systems, e.g. copper fluoroborate; substituted phenolics, and tertiary amines, such as imidazole, 2,4,6-tri(dimethylaminomethyl)phenol, and benzyldimethylamine.

The following examples are intended to illustrate various embodiments of the invention and are not intended to restrict the scope thereof.

EXAMPLE 1

Preparation of Epoxy Resins

A series of epoxy resins was prepared in conventional manner using various amine curing agents. The formulations were made with commercial epoxy resins including D.E.R. 383 (Dow), Epon 826 and Epon 828 (both by Shell). The formulations were cured with stoichiometric levels of curing agents. Both commercial amine curatives and blends containing the MPCA poly(cyclohexyl-aromatic)amines were compared. The blend containing the MPCA obtained by the hydrogenation of crude methylenedianiline and partial distillation thereof (hereinafter referred to as "MPCA Blend") comprised the following components and amounts:

5.0% di(4-aminocyclohexyl)methane; (PACM)
0.5% 4-aminocyclohexyl-4-hydroxycyclohexyl methane;
5.4% 4-(4'-aminobenzyl)cyclohexylamine; (ABCHA)
17.9% 2,4-di(4-aminocyclohexylmethyl)cyclohexylamine;
49.8% 2,4-di(4-aminocyclohexylmethyl)aniline;
6.5% 4,4'-di(4-aminocyclohexylmethyl)dicyclohexylamine;
7.5% partially hydrogenated trimethylenetraaniline and analogs thereof; and
7.4% non elutables.

The polyepoxides and amine curatives as described above were mixed at temperatures between 25° and 50° C. Entrained air was removed by one of two methods: 1) by applying a vacuum for about 1-15 minutes until foaming stopped indicating most of the air had been removed, or 2) by placing the mixture in a centrifuge until the mixture of polyepoxide and curative was clear. After removal of the entrained air, the mixture of amine curative and polyepoxide was poured into ⅛ inch molds preheated to 80° C. for the elevated cure systems. The elevated cure systems were placed in an 80° C. circulating air oven and cured at that temperature for 2 hours and then for 3 hours at 150° C. Molds were allowed to cool to room temperature and the ⅛ inch castings were removed. Samples of the resulting resin were prepared for mechanical and physical testing. The mechanical and physical properties then were determined by standard methods. The results are set forth in Table 1.

TABLE 1

PROPERTIES OF DGEBA HEAT CURED SYSTEMS

| PROPERTIES | AMICURE PACM | ANCAMINE 2049 | MDA | MPCA* | 50/50 PACM/MPCA* |
|---|---|---|---|---|---|
| VISCOSITY | | | | | |
| @ 25° C. (CPS) | 80 | 112 | Solid | — | 2175 |
| @ 40° C. (CPS) | — | — | — | 60,000 | — |
| EQ. WEIGHT | 52.5 | 59.5 | 50 | 55.1** | 54** |
| FORMULAITON VISCOSITY (CPS) | | | | | |
| @ 25° C. | 4250 | 5345 | — | — | 6250 |
| @ 40° C. | — | — | — | 3730 | — |
| @ 60° C. | 250 | 220 | 170 | — | — |
| GEL TIME (MIN) | | | | | |
| @ 25° C. | 175 | 295 | >8 HRS | — | — |
| @ 40° C. | — | — | — | 94 | — |
| @ 60° C. | 27 | 59 | — | — | — |
| @ 80° C. | 9 | — | 93 | — | — |
| DSC REACTIVITY | | | | | |
| ONSET °C. | 88 | — | 130 | 87 | 89 |
| PEAK °C. | 116 | — | 163 | 118 | 119 |
| ΔH (J/g) | 447 | — | 300 | 437 | 457 |
| Tg °C. | 156 | 150 | 160 | 182 | 175 |
| MECHANICAL PROPERTIES | | | | | |
| TENSILE STRENGTH (MPa) | 71.6 | 69.6 | 70.3 | 56.5 | 71.0 |
| TENSILE MODULUS (MPa) | 2240 | 2412 | 3164 | 2572.8 | 2516.3 |
| % ELONGATION | 5.5 | 3.8/ 4.0 | 3.0 | 4.6 | — |
| FLEXURAL STRENGTH (MPa) | 164.7 | 146.5 | 175.8 | — | — |
| FLEXURAL MODULUS (MPa) | 3522 | 3558.4 | 3440.1 | — | — |
| FRACTURE TOUGHNESS GIC kJ/M$^2$ | 0.29 | 0.22 | 0.22 | — | — |
| CHEMICAL RESISTANCE % WT GAIN AFTER 120 DAYS) | | | | | |
| ACETONE | 8.51 | 16.52 | 10.69 | 5.64 | — |
| TOLUENE | 0.66 | 0.33 | 0.24 | 0.73 | — |
| ETHANOL | 1.20 | 1.47 | 0.83 | 0.51 | — |
| METHANOL | — | — | — | 5.21 | — |
| AMMONIUM HYDROXIDE, 10% | 4.20 | 1.59 | 1.65 | 1.81 | — |
| SODIUM HYDROXIDE, 10% | — | — | — | 1.48 | — |
| NITRIC ACID, 10% | 7.42 | 5.72 | 0.89 | 3.64 | — |
| ACETIC ACID, 25% | 16.6 | 12.95 | 1.44 | 6.73 | — |
| SULFURIC ACID, 30% | — | — | — | 2.16 | — |

TABLE 1-continued

| | PROPERTIES OF DGEBA HEAT CURED SYSTEMS | | | | |
|---|---|---|---|---|---|
| PROPERTIES | AMICURE PACM | ANCAMINE 2049 | MDA | MPCA* | 50/50 PACM/MPCA* |
| DI WATER | 1.97 | 1.65 | 1.64 | 1.71 | — |

DGEBA polyepoxide is a diglycidyl ether of bisphenol A epoxy having an epoxide equivalent weight between 176 and 192.
ANCAMINE 2049 is a trademark of Air Products and Chemicals, Inc. identifying dimethyl PACM.
AMICURE PACM is a trakemark if Air Products and Chemicals, Inc. identifying PACM.
MDA is methylenedianiline.
*MPCA cured D.E.R. 383, all others cured Epon 828.
**Exact eq. weight depends upon the composition of MPCA.

EXAMPLE 2

Preparation of Epoxy Resins

A series of heat cured epoxy resins was synthesized in accordance with the procedure of Example 1. The MPCA Blend of Example 1 was combined with additional amounts of other aliphatic and cycloaliphatic-aromatic amine curatives. The results of physical and mechanical tests are shown in Tables 2 and 3.

organic solvents than do the PACM, ANCAMINE 2049 curative and MDA cured resins. In many instances the chemical resistance approached that of the aromatic amine, MDA, but the mechanical properties approached those of the cycloaliphatic amines, i.e., PACM and ANCAMINE 2049 curatives. Gel times for the MPCA cured epoxy resin were significantly shorter than those obtained with MDA. The mixture of PACM and MPCA provided benefits intermediate to those of

TABLE 2

| | PROPERTIES OF DGEBA HEAT CURED SYSTEMS | | | | |
|---|---|---|---|---|---|
| CURATIVE | 50% MPCA 50% ABCHA | 33.3% MPCA 33.3% ABCHA 33.3% PACM | 70% MPCA 17% ABCHA 13% PACM | 40% MPCA 60% DETDA | ABCHA |
| VISCOSITY @ 25°C. (CPS) | semi-solid | 3072 | 17,380 | 2820 | solid |
| FORMULATION VISCOSITY (CPS) @ 25° C. | — | 7143 | 11,600 | 10,700 | — |
| GEL TIME (MIN) | | | | | |
| @ 25° C. | — | 181 | 170 | — | — |
| @ 40° C. | — | 291 | 80 | — | — |
| DSC REACTIVITY | | | | | |
| ONSET C | 79 | 83 | 84 | 79 | 77.5 |
| PEAK C | — | — | — | 127/184 | — |
| ΔH (J/g) | 410 | 426 | 388 | 363 | 437 |
| Tg C | 175 | 166 | 167 | 184 | 169 |
| MECHANICAL PROPERTIES | | | | | |
| TENSILE STRENGTH (MPa) | — | — | — | 71.70 | 77.9 |
| TENSILE MODULUS (MPa) | — | — | — | 2640 | 2295 |
| % ELONGATION | — | — | — | 5.1 | 5.8 | cured for 2 hrs @ 80° C. followed by 3 hrs at 150° C.
MPCA refers to the MPCA Blend of Example 1.
ABCHA refers to 4-(4'aminobenzyl)cyclohexylamine.
DETDA refers to diethyltoluenediamine.

TABLE 3

| | PROPERTIES OF DGEBA HEAT CURED SYSTEMS | | | |
|---|---|---|---|---|
| CURATIVE | 66.7% ABCHA 13.3% PACM 20% MPCA | 66.7% MPCA 33.3% ABCHA | 80% PACM 20% MPCA | 50% PACM 60% MPCA |
| VISCOSITY @ 25° C. (CPS) | semi-solid | 84820 | 208 | 3772 |
| FORMULATION VISCOSITY (CPS) @ 25° C. | — | 17300 | 2340 | 7340 |
| GEL TIME (MIN) | | | | |
| @ 25° C. | — | — | — | 183 |
| @ 40° C. | — | — | 142 | 122 |
| DSC REACTIVITY | | | | |
| ONSET °C. | 79 | 83 | 88 | 85 |
| PEAK °C. | 115 | 118 | 115 | 118 |
| ΔH (J/g) | 410 | 411 | 442 | 429 |
| Tg °C. | 167 | 178 | 164 | 171 |
| MECHANICAL PROPERTIES** | | | | |
| TENSILE STRENGTH (MPa) | 75.8 | 64.1 | 75.8 | 62.0 |
| TENSILE MODULUS (MPa) | 2295 | 2516 | 2564 | 2550 |
| % ELONGATION | 3.0 | 3.6 | 5.2 | 4.1 |

The above results in Tables 1–3 from Examples 1 and 2 show that the MPCA cured resin generally has significantly better chemical resistance to many conventional organic solvents than PACM and MPCA alone. Formulating a curative based on PACM and MPCA offers a processing benefit with respect to viscosity and reactivity while retaining many of the benefits offered by MPCA with respect to chemical resistance and mechanical properties.

The MPCA Blend of Example 1 with additional amounts of PACM, ABCHA, and both, as noted in Table 3, offered excellent physical properties.

EXAMPLE 3

Resistance to Caustic Using Epoxy Resin Formulations Based On High Molecular Weight Polyepoxides The procedure of Example 1 was repeated except that the Epon 830, another resin marketed by Shell, resin was substituted for the Epon 828. The test samples were exposed to a 10% sodium hydroxide solution for 7 days at 75° C. Properties are set forth in Table 4.

TABLE 4

SOIDUM HYDROXIDE RESISTANCE
FOR PACM/MPCA AND PACM CURED EPON 830

| PROPERTIES | 50/50 PACM/ MPCA CURED EPON 830* | PACM CURED EPON 830* |
| --- | --- | --- |
| STORAGE MODULUS (E'), MPa (BEFORE IMMERSION) | 2762 | 2630 |
| STORAGE MODULUS (E'), MPa (AFTER IMMERSION) | 2691 | 2546 |
| AVERAGE % DROP IN MODULUS | 2.6 | 3.2 |
| GLASS TRANSITION (Tg), °C. (BEFORE IMMERSION) | 156 | 146 |
| GLASS TRANSITION (Tg), °C. | 143 | 134 |
| AVERAGE % DROP IN GLASS TRANSITION TEMPERATURE | 8.22 | 8.28 |
| % WEIGHT CHANGE AFTER IMMERSION | +1.332 | +1.349 |

*CURED 2 HOURS @ 80° C., FOLLOWED BY 3 HOURS @ 150° C.

The data in Table 4 shows that the mixture of PACM and MPCA gave improved retention of modulus and thermal properties after exposure to dilute caustic, demonstrating improved chemical resistance compared to PACM alone.

EXAMPLE 4

Low Temperature Cured Epoxy Resin

Test coatings for use in coatings and civil engineering applications were prepared in conventional manner using the MPCA amine curative of Example 1. More particularly, the formulation comprised the following: 90 parts of D.E.R. 351 blend of bisphenol A and bisphenol F diglycidyl ether and 10 parts of Epodil $C_{12-14}$ glycidyl ether by weight cured with a stoichiometric amount of test amine curative. Table 5 below sets forth the results for films cured at 10° and 25° C. cure temperatures.

TABLE 5

Low Temperature Cured Epoxy Resins

| CURATIVE | 1888 | 2257 | DB272 MXA1[1] | DB272 MXA2[2] |
| --- | --- | --- | --- | --- |
| VISCOSITY @ 25° C./CPS | 5300 | 840 | 140 | 220 |
| MIXED VISCOSITY @ 25° C./CPS | 14700 | 800 | 380 | 480 |
| COLOR GARDNER | 12 | 8 | 6 | 6 |
| GEL TIME @ 25° C./MIN | 24 | 32 | 31 | 35 |
| PEAK EXOTHERM @ 25° C. | 145 | 114 | 153 | 155 |
| TIME TO PEAK EXOTHERM/MIN | 30 | 39 | 40 | 42 |
| LOADING/PHR | 60 | 65 | 50 | 50 |
| CARBAMATION RESISTANCE/DAYS: (NOTE: ALL LEVELS OF CARBAMATION WERE VERY LOW IF PRESENT AT ALL) | | | | |
| @ 10° C. | 0 | 1-2 | 2-3 | 3-4 |
| @ 25° C. | 0 | 0 | 0-1 | 1 |
| CONICAL MANDREL ELONGATION/% | <2 | <30 | <30 | <30 |
| DIRECT IMPACT RESISTANCE/KG.M | 1.04 | <1.80 | 0.90 | 1.22 |
| REVERSE IMPACT RESISTANCE/KG.M | 0.018 | 0.36 | 0.108 | 0.19.8 |

1888 is a mixture of methylenedianiline, 20% Epon 828, 6% Cardura E-10, 19% benzyl alcohol, and 49% salicyclic acid.
2257 is a mixture of 50% of the MPCA Blend of Example 1, 45% benzyl alcohol, and 5% salicylic acid.
[1] is the MPCA Blend of Example 1 in an amount of 33% by weight, 1,3-xylylenediamine in an amount of 18%, bisphenol A 5%, and benzyl alcohol in an amount of 44%.
[2] is the MPCA Blend of Example 1 in an amount of 4.15% by weight, 1,3-xylylenediamine in an amount of 13.5%, bisphenol A 3.5%, and benzyl alcohol in an amount of 41.5%.

The results show that epoxy resins cured at subambient temperature with the MPCA blend of Example 1 did not suffer from surface carbamate contamination. The MPCA Blend when used alone or in combination with meta xylylene diamine, provides effective cure of epoxy resin, good resistance to surface carbamation, and good application viscosity.

EXAMPLE 5

Ambient Cured Castings

The procedure of Example 1 was repeated, except that mixtures of the amine curative and polyepoxide were cured at ambient temperature in the molds for seven days before the castings were removed. Table 6 sets forth the results of the tests.

TABLE 6

| PROPERTIES OF DGEBA AMBIENT CURED SYSTEMS | | | | |
|---|---|---|---|---|
| CUREING AGENTS | 2280 | 1884 | 1693 | MCA |
| VISCOSITY @ 25° C./CPS | 500 | 300 | 150 | 150 |
| COLOR (GARDNER) | 8 | 2 | 3 | 3 |
| USE LEVEL (PHR) | 60 | 45 | 50 | 55 |
| GEL TIME (MIN) | 50 | 70 | 50 | 30 |
| COMPRESSIVE STRENGTH (MPA) | 7.15 | 92.4 | 69.2 | 85.2 |
| CHEMICAL RESISTANCE* | | | | |
| XYLENE | 0.1 | 2.3 | 1.0 | 0.4 |
| TOLUENE | 2.3 | DESTROYED | 6.6 | 3.3 |
| BUTYL CELLOSOLVE | 2.4 | 6.2 | 2.5 | 6.5 |
| ETHANOL | 6.9 | 5.2 | 5.0 | 10.7 |
| SKYDROL 500 | −0.3 | | −0.3 | −0.1 |
| D.I. WATER | 1.2 | 0.8 | 1.1 | 0.9 |
| 10% ACETIC ACID | 5.4 | 12.2 | 4.6 | 5.0 |
| 10% LACTIC ACID | 1.9 | 8.7 | 1.7 | 2.5 |
| 70% SULFURIC ACID | 0.2 | 1.0 | 0.0 | 0.2 |
| 50% NAOH | −0.2 | −0.1 | −0.2 | −0.2 |

Samples immersed 21 days at ambient temperature.
2280 is the MPCA Blend of Example 1 with benzyl alcohol and salicylic acid.
1884 is a 1,2-cyclohexanediamine-epoxy adduct modified with polyoxypropylene amine and benzyl alcohol.
1693 is a 1,2-cyclohexanediamine adduct modified with benzyl alcohol.
MCA is a mannich base of isophoronediamine with phenol and formaldehyde, modified with benzyl alcohol.

The above results show that the MPCA cured resin has significantly better chemical resistance especially against hydrocarbons such as xylene and toluene.

What is claimed is:

1. In a polyepoxide resin comprising the reaction product of a polyglycidyl polyether of a polyhydric alcohol having terminal 1,2 epoxy groups cured with a polyamine curative, the improvement which comprises the incorporation of a methylene bridged poly(cyclohexyl-aromatic)amine mixture designated MPCA, wherein the MPCA contains 3 ring and higher ring components, represented by the formula:

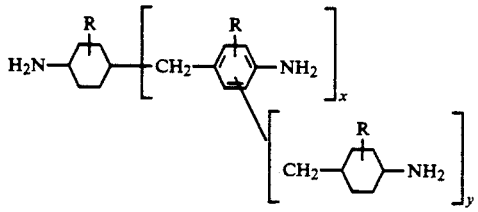

wherein R is hydrogen or methyl, x is 1–3 and y is 0–2 and the sum of x and y is from 2 to 4.

2. The polyepoxide resin of claim 1 wherein R in the MPCA curative is hydrogen.

3. The polyepoxide resin of claim 2 wherein the weight ratio of the 3 ring component to higher ring components in said MPCA is from 50 to 90 weight parts of the 3 ring component per 10 to 50 weight parts of higher ring components.

4. The polyepoxide resin of claim 3 wherein the ratio of cycloaliphatic rings to aromatic rings in said MPCA is from 0.5 to 2:1.

5. The polyepoxide resin on claim 4 wherein the ratio of cycloaliphatic rings to aromatic rings in said MPCA is from 1.3 to 1.9:1.

6. The polyepoxide resin of claim 3 wherein the MPCA, as determined by gas chromatographic analysis, comprises the following weight percentages:
10–37% 2,4-di(4-aminocyclohexylmethyl)cyclohexylamine;
67–85% 2,4-di(4-aminocyclohexylmethyl)aniline;
0–20% 4,4'-di(4-aminocyclohexylmethyl)dicyclohexylamine; and,
5–14% partially hydrogenated mixture of trimethylenetetraaniline and higher molecular weight aniline oligomers.

7. The polyepoxide resin of claim 2 wherein the MPCA is present as a partially distilled hydrogenation product and comprises the following:
2–10% di(4-aminocyclohexyl)methane;
0.5–2% 4-aminocyclohexyl-4-hydroxycyclohexyl methane;
5–17% 4-(4'-aminobenzyl)cyclohexylamine;
5–25% 2,4-di(4-aminocyclohexylmethyl)cyclohexylamine;
35–55% 2,4-di(4-aminocyclohexylmethyl)aniline;
0–15% 4,4'-di(4-aminocyclohexylmethyl)dicyclohexylamine; and,
3–8% partially hydrogenated mixture of trimethylenetetraaniline and higher molecular weight aniline oligomers.

8. The polyepoxide resin of claim 7 wherein the amine hydrogen equivalent of said MPCA is from 50–60.

9. The polyepoxide resin of claim 2 wherein the polyglycidyl ether of a polyhydric alcohol is a polyglycidyl ether of a polyhydric phenol and the ratio of amine curative to the polyglycidyl ether of a polyhydric phenol is 0.6–1.7 amine hydrogens per epoxide equivalent of the polyglycidyl polyether of a polyhydric phenol.

10. The polyepoxide resin of claim 9 wherein the polyglycidyl ether of a polyhydric phenol is a polyglycidyl ether of bisphenol A.

11. The polyepoxide resin of claim 9 wherein the curative comprises from 5–70 percent of MPCA by weight and from 30 to 95% by weight of an additional polyamine curative.

12. The polyepoxide resin of claim 11 wherein the additional polyamine is isophoronediamine.

13. The polyepoxide resin of claim 11 wherein the additional polyamine is di(4-aminocyclohexyl)methane.

14. The polyepoxide resin of claim 11 wherein the additional polyamine is 1,3-xylylenediamine.

15. The polyepoxide resin of claim 11 wherein the additional polyamine is 4-(4'-aminobenzyl)cyclohexylamine.

16. The polyepoxide resin of claim 11 wherein the curative comprises 15-70% MPCA, and from 30 to 85% by weight of di(4-aminocyclohexyl)methane, 4-(4'-aminobenzyl)cyclohexylamine or combinations thereof.

17. In a process for forming an epoxy resin by reacting a polyglycidyl ether of a polyhydric phenol with a polyamine curative wherein the ratio of polyglycidyl ether of a polyhydric phenol to polyamine curative is from 0.6-1.7 amine hydrogens per epoxide equivalent of polyglycidyl ether of a polyhydric phenol, the improvement which comprises utilizing a polyamine curative mixture designated MPCA, wherein the MPCA contains 3 ring and higher ring components, represented by the formula:

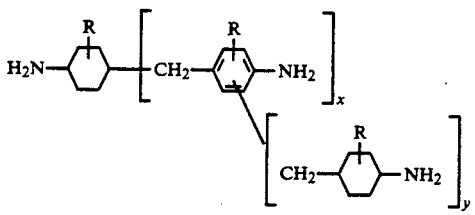

wherein R is hydrogen or methyl, x is 1-3 and y is 0-2 and the sum of x and y is from 2 to 4 as at least a portion of said polyamine curative.

18. The process of claim 17 wherein R in the MPCA curative is hydrogen.

19. The process of claim 18 wherein the weight ratio of the 3 ring component to higher ring components in said MPCA is from 50 to 90 weight parts of the 3 ring component per 10 to 50 weight parts of higher ring components.

20. The process of claim 19 wherein the ratio of cycloaliphatic rings to aromatic rings in said MPCA is from 0.5 to 2:1.

21. The process of claim 20 wherein the ratio of cycloaliphatic rings to aromatic rings in said MPCA is from 1.3 to 1.9:1.

22. The process of claim 20 wherein the MPCA, as determined by gas chromatographic analysis, comprises the following weight percentages:
10-37% 2,4-di(4-aminocyclohexylmethyl)cyclohexylamine;
67-85% 2,4-di(4-aminocyclohexylmethyl)aniline;
0-20% 4,4'-di(4-aminocyclohexylmethyl)dicyclohexylamine; and,
5-14% partially hydrogenated mixture of trimethylenetetraaniline and higher molecular weight aniline oligomers.

23. The process of claim 18 wherein the MPCA is present as a partially distilled hydrogenation produce and comprises the following:
2-10% di(4-aminocyclohexyl)methane;
0.5-2% 4-aminocyclohexyl-4-hydroxycyclohexyl methane;
5-17% 4-(4'-aminobenzyl)cyclohexylamine;
5-25% 2,4-di(4-aminocyclohexylmethyl)cyclohexylamine;
35-55% 2,4-di(4-aminocyclohexylmethyl)aniline;
0-15% 4,4'-di(4-aminocyclohexylmethyl)dicyclohexylamine; and,
3-8% partially hydrogenated mixture of trimethylenetetraaniline and higher molecular weight aniline oligomers.

24. The process of claim 23 wherein the amine hydrogen equivalent of said MPCA is from 50-60.

25. The process of claim 18 wherein the polyglycidyl ether of a polyhydric phenol is a polyglycidyl ether of bisphenol A.

26. The process of claim 18 wherein the curative comprises from 5-70 percent of MPCA by weight and 30 to 95% by weight of an additional polyamine curative.

27. The process of claim 26 wherein the additional polyamine is isophoronediamine.

28. The process of claim 26 wherein the additional polyamine is di(4-aminocyclohexyl)methane.

29. The process of claim 26 wherein the additional polyamine is 1,3-xylylenediamine.

30. The process of claim 26 wherein the additional polyamine is 4-(4'-aminobenzyl)cyclohexylamine.

31. The process of claim 26 wherein the curative comprises 15-70% MPCA and from 30-85% by weight of di(4-aminocyclohexyl)methane, 4-(4'-aminobenzyl)cyclohexylamine or combinations thereof.

* * * * *